United States Patent [19]
Antoniol et al.

[11] Patent Number: 5,708,429
[45] Date of Patent: Jan. 13, 1998

[54] METHOD OF COMPRESSING ELECTROENCEPHALOGRAPHIC SIGNALS

[75] Inventors: Giuliano Antoniol, Pergine; Paolo Tonella, Ravina, both of Italy

[73] Assignee: Istituto Trentino Di Cultura, Trento, Italy

[21] Appl. No.: 588,683

[22] Filed: Jan. 19, 1996

[30] Foreign Application Priority Data

Jan. 26, 1995 [IT] Italy ................................ TO95A0051

[51] Int. Cl.$^6$ ..................................... H03M 7/40
[52] U.S. Cl. ................. 341/65; 341/67; 128/731
[58] Field of Search .................. 341/65, 67; 128/731

[56] References Cited

PUBLICATIONS

Computer Methods and Programs in Biomedicine, vol. 30, No. 4, Dec. 1, 1989, Netherlands, pp. 207–217, XP000571006, B. Lütkenhöner: "A Suboptimum Variable–Length Encoding Procedure for Discrete Quantizided Data".

Annals of Biomedical Engineering, vol. 19, No. 1, 1991, US, pp. 1–14, XP000570999, Nicoletti et al: "The Application of Delta Modulation to EEG Waveforms for Database Reduction and Real Time Signal Processing".

Proceedings of the Thirteenth Annual Northeast Bioengineering Conference, vol. 2, Mar. 12–13, 1987, PA, US, pp. 632–635, XP000568097, Wawrzynski et al: "Interactive Coder Workstation for Compression and Processing of EEG Waveforms".

International Journal of Bio–Medical Computing, vol. 35, No. 3, Apr. 1, 1994, pp. 207–217, XP000433047, Pradhan et al: "Data Compression by Linear Prediction for Storage and Transmission of EEG Signals".

*Primary Examiner*—Brian K. Young
*Attorney, Agent, or Firm*—Sughrue, Mion, Zinn, Macpeak & Seas, PLLC

[57] ABSTRACT

In a method of compressing electroencephalographic signals, the signals are compressed by the encoding of the differences between values of the signal and values estimated by a predictor with the use of variable-length codes with prefixes.

12 Claims, 2 Drawing Sheets

ENCODER

| INPUT | OUTPUT |
|---|---|
| 00000000 | 1 |
| 00000001 | 00 |
| 00000010 | 011 |
| 00000011 | 1001 |
| 00000100 | 110 |
| ...... | ...... |

DECODER

METHOD OF COMPRESSING ELECTROENCEPHALOGRAPHIC SIGNALS

BACKGROUND OF THE INVENTION

The present invention relates in general to methods of compressing signals and, more specifically, relates to a method of compressing electroencephalographic signals to enable them to be stored and/or transmitted with consequent reductions in mass storage and/or pass-band.

The object of the present invention is to provide a compression method which achieves greater efficiency and convenience of use than the methods of the prior art.

According to the present invention, this object is achieved by virtue of a compression method having the characteristics indicated in the claims which follow the present description.

Further advantages and characteristics of the present invention will become clear from the following detailed description provided by way of non-limiting example.

The compression of electroencephalographic signals, known as EEGs for short, according to the present invention makes use of the fact that these signals are typically of limited differential. This means that the amount of information carried by the differential is less than that carried by the signal and it is thus possible to use a smaller number of bits to encode it. The principle upon which the invention is based is therefore to encode the differential rather than the signal and then to reconstruct the signal from the differential at the decoding stage.

Electroencephalographic signals are typically signals with limited first differential; that is, they are signals which vary slowly in time. Moreover, there is always a background noise of small magnitude superimposed on the signal. These characteristics of EEG signals make it easy to make an approximate prediction of the subsequent value of the signal, given the preceding values.

It is possible to speak of values of the signal since the present invention relates to the processing of signals which are in digital format and which, typically, can therefore assume a finite number of discrete values. EEG signals, which are originally analog signals, therefore have to be converted beforehand into digital format, that is, into sequences of binary numerals or bits. This operation, however, is widely known and very widespread in the art. In the specific case, EEG signals are therefore ordered sequences of discrete values in digital format.

The most simple prediction which can be formulated is that $p(n+1)=x(n)$ where $x(n)$ is the current value of the signal and $p(n+1)$ is the predicted subsequent value. If the Markov matrix constituted by the conditioned probabilities $P[x(n+1)|x(n)]$ is estimated on a sufficiently large database, it can be observed that it assumes the maximum values along the principal diagonal. This confirms the good quality of the prediction $p(n+1)=x(n)$ since it is the same as would be formulated by a Markovian predictor.

On the basis of the foregoing, it is clear that the difference $x(n+1)-p(n+1)$ is concentrated around zero; this is in line with the initial statement that the signals are of limited differential, since the difference $x(n+1)-p(n+1)$ is equal to $x(n+1)-x(n)$, and is therefore a discretization of the differential. Given an EEG signal, there is therefore a very large number of differences between the value predicted and the actual value and these differences are concentrated around zero.

It is therefore possible to use an encoding system, commonly known as a code, in the method of compressing EEG signals. So-called variable-length codes, which are widely known in the art, enable short code words to be used for the more frequent symbols and long code words for the less frequent symbols. They enable good levels of compression to be achieved if the frequencies of the symbols are characterized by very high values on a small subset of symbols and by low values on the other symbols. Since, in this case, the values of $p(n+1)-x(n+1)$ which are close to 0 are characterized by a high frequency, whilst the values far from 0 are rare, the use of existing variable-length codes is extremely profitable.

Of the various variable-length codes existing, codes with prefixes are particularly advantageous. The basic property of codes with prefixes consists of the fact that two distinct code words in which one is the prefix of the other do not exist. This means that it is possible to recognize a code word without knowing beforehand how long it is since a scanning from left to right of the bits which constitute it cannot at the same time satisfy one code word and the prefix of another so that there is no ambiguity in recognition.

On the other hand, it is not restrictive to consider only codes with prefixes since it can be shown that the optimal compression achievable with a code oriented to the character is always obtainable even with a code with a prefix.

DESCRIPTION OF THE PREFERRED EMBODIMENTS

Figures 1, 2:
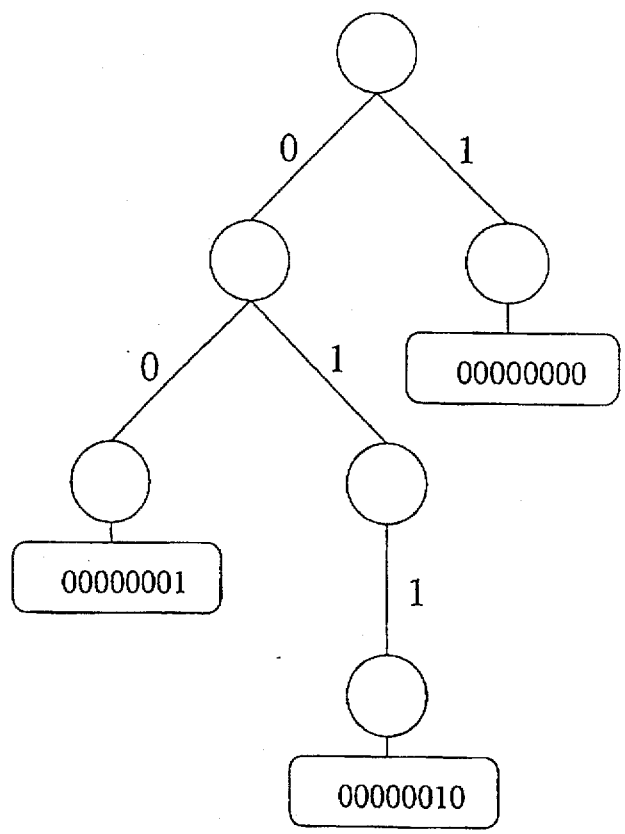
FIG. 1 is an input/output table of the encoding scheme of the present invention.
FIG. 2 is an decoder flow chart of the decoding scheme of the present invention.
Figure 3:
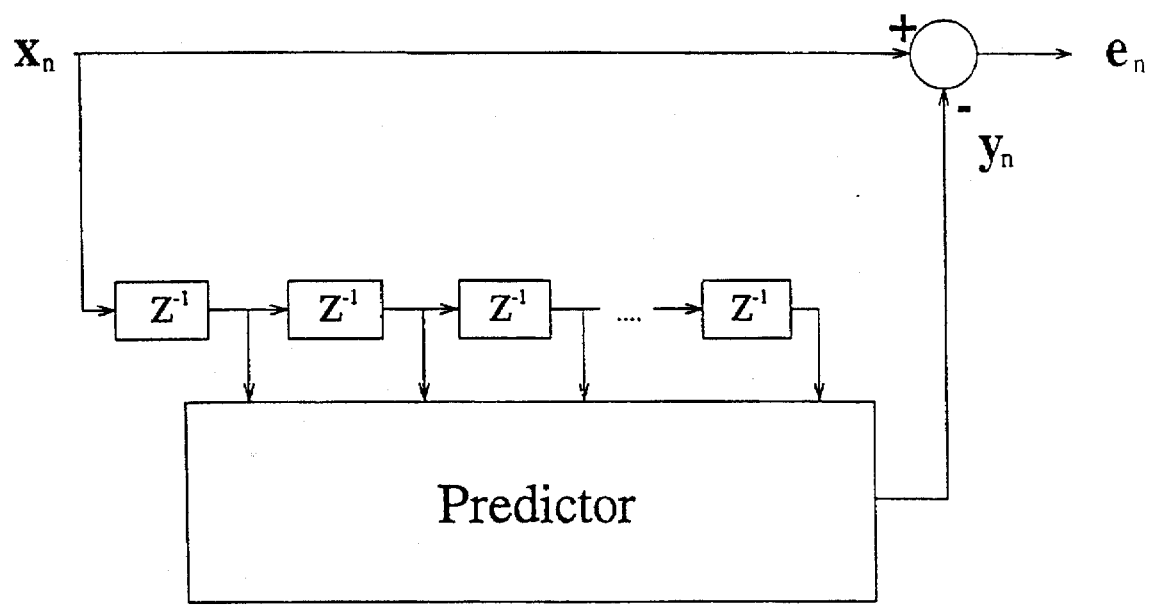
FIG. 3 is block diagram of the signal transformation based on the predictive scheme of the present invention.

The algorithm selected in the specific embodiment which is currently considered preferable for encoding $x(n+1)-p(n+1)$ by means of a code with a prefix is Huffman's algorithm; it is based on a data structure with a priority queue. A priority queue is a data structure known in the art in which the extraction operation always provides the item with the smallest key value; typically the priority queues are formed by means of heaps.

A heap is a data structure known in the art in which the items contained are organized in a binary tree for which the following characteristic applies:

"for each node of the tree (other than the root) the key value is greater than or equal to the key value of the parent node".

Clearly, in order to produce a priority queue from a heap it suffices to implement the extraction of an object as the extraction of the root and to reset the heap characteristic.

The EEG signal to be compressed is indicated $X=\{x(1), x(2), \ldots, x(N)\}$; the symbols $x(i)$ belong to the discrete set of possible values produced by the sampling or conversion into digital format, $Q=\{0, 1, 2, \ldots, M\}$ so that the differences $p(n+1)-x(n+1)$ belong to the discrete set $D=\{-M, \ldots, -1, 0, 1, \ldots, M\}$ where the following is true for the cardinalities:

$$\#D = 2\#Q-1 = 2M+1$$

H indicates a priority queue of items of the type:

(freq, symbol, sx, dx)

that is, data structures comprising the elements freq, symbol, sx, dx, where symbol belongs to D and freq is the frequency with which the symbol is present in the vector Y of the differences; sx and dx are two pointers which identify the two progeny of the node in question.

This queue uses the frequency freq as a key.

tab[i] (i belongs to D) indicates the conversion (or encoding) table which associates with each symbol of D a string of bits which encodes that symbol. In a currently-preferred embodiment, this conversion table tab[i] is associated with the sequence of symbols constituting the EEG signal compressed by the method according to the present invention so as to enable it to be decompressed easily. The various compression steps of the method according to the present invention can therefore be represented in greater detail as follows:

```
1) Calculate the vector of the differences Y:
   for i = 1 , . . . , N-1
       y(i) = x(i+1) - x(i)
2) Calculate the frequencies of the symbols in Y:
   for i = -M, . . . , M
       freq[i] = 0
   for i = 1 , . . . , N-1
       freq[y(i)] = freq[y(i)] + 1
3) Insert the symbols of Y in the priority queue H
   having the frequency as a key:
   for i = -M, . . . , M
       insert { H, (freq[i], i, NIL, NIL) }
4) Construct the binary tree B from the priority queue H:
   for i = 1 , . . . , 2M
       n = new node ()
       n.sx = extract { H }
       n.dx = extract { H }
       n.freq = n.sx.freq + n.dx.freq
       insert { H, n }
   B = extract { H }
5) Traverse the tree B in pre-order thus constructing
   the conversion table tab;
   preord procedure (node n)
   start
   if n is a leaf
       tab[n.symbol] = string
       string = ""
   otherwise
       loc_str = string
       string = loc_str + "0"
       preord (n.sx)
       string = loc_str + "1"
       preord (n.dx)
   end
6) Create a compressed file including therein the table
   used for the encoding and the initial value of the
   signal:
   for i = -M, . . . , M
       write { tab[i] }
   write { x(1) }
   for i = 1, . . . , N-1
       write { tab [y(i)] }
```

The corresponding decompression steps can be represented as follows:

```
1) Reconstruct the binary tree B from the encoding
   table tab:
   m = B
   for i = -M, . . . , M
       for j = 1, . . . , length (tab[i])
           n = new_node ()
           n.sx = NIL
           n.dx = NIL
           n.symbol = NIL
           if character ( tab[i], j) = "0"
               m.sx = n
               m = m.sx
           otherwise
               m.dx = n
```

-continued
```
               m = m.dx
       m.symbol = i
       m = B
2) Decode each string of bits input by traversing the
   tree B:
   for i = 1, . . . N-1
       read { string }
       m = B
       for j = 1, . . . , length (string)
           if character (string, j) = "0"
               m = m.sx
           otherwise
               m = m.dx
       y(i) = m.symbol
3) Reconstruct the signal X from Y:
   for i = 1 , . . . , N-1
       x(i+1) = x(i) + y(i)
```

Naturally, compression and decompression methods using similar data structures having a substantially similar sequence of steps are possible.

The embodiment of the method of compressing electroencephalographic signals described above is optimized for each individual trace since the optimal table for encoding the differential is constructed on the basis of the statistic of the differential of that specific trace.

The speed of carrying out the method can be increased considerably if an average encoding table is used in place of the optimal encoding table for a given trace. It has been found by means of tests carried out on a database by the Applicant that the use of an average table involves a minimal loss of compression capacity (changing from an average compression of 58.4% to a compression of 57.6%) but permitting a considerable gain in terms of execution times.

The use of an average encoding table also enables the encoding (and hence also the transmission or storing) of the signal to be carried out whilst the signal is being acquired without the need to have the whole signal available before being able to evaluate its differential and from it the encoding table. This advantageous embodiment of the method according to the invention will now be described.

$X=\{x(1), x(2), \ldots, x(N)\}$ indicates the EEG signal to be compressed; the symbols $x(i)$ belong to the discrete set of possible values produced by the sampling $Q=\{0, 1, 2, \ldots M\}$ for which the differences $p(n+1)-x(n+1)$ belong to the discrete set $D=\{-M, \ldots, -1, 0, 1, \ldots M\}$ where the following formula applies for the cardinalities:

$$\#D = 2\#Q - 1$$

The database available for the evaluation of the compression method is divided into two subsets which constitute divisions thereof. The first subset referred to below as the training set is used to determine the average statistics of the frequencies of the symbols which appear in the differential. The second subset referred to as the test set is used to estimate the decay in performance which takes place upon changing from the set of data from which the encoding table was constructed (the training set) to a completely new set of data. The table of average frequencies with which the symbol i appears in the training set is indicated freq[i] (i belongs to D).

The steps 3, 4, 5 of the compression method described above are then applied to the vector of the average frequencies freq[i] thus obtaining an average compression table which is indicated tab[i] (i belongs to D), which associates with each symbol of D the string of bits which encodes that symbol.

A table of this type was calculated with the use of a training set constituted by 96 traces. It was then applied to a test set comprising 58 traces in order to evaluate the decay in performance resulting from the application of this table to completely new data. The compression ratio expressed by:

$$comp = (L_{ini} - L_{fin})/L_{ini}$$

where $L_{ini}$ and $L_{fin}$ represent the length of the trace before and after compression was considered as an index of the performance. The average compression ratio on the training set was equal to 58.4% against a compression ratio of 57.6% on the test set with a decay in performance which is wholly negligible, particularly in relation to the considerable advantages resulting from the use of this faster embodiment of the compression method according to the invention. These advantages consist basically of the shorter calculation time required for the encoding and of the fact that it is possible to compress the data immediately after its acquisition.

This embodiment will now be described in greater detail for a better understanding. In a data structure of the binary tree type, indicated B, each node contains the following information:

(symbol, sx, dx)

in which symbol belongs to D and sx and dx are two pointers which identify the left-hand and right-hand progeny of the node in question.

The various compression steps can be summarized as follows:

```
1. Include in the compressed file (or transmit) the
   initial value of the signal:
   write/transmit { x(1) }
2. Calculate the difference y and encode it with
   tab[y]:
   for i = 1 , . . . , N-1
      y = x(i+1) - x(i)
      write/transmit { tab[y] }
```

The various decompression steps can be summarized as follows:

```
1. Construct the binary tree from the encoding table
   tab:
   m = B
   for i = -M, . . . , M
   for j = 1, . . . , length (tab[i])
      n = new node ()
      n.sx = NIL
      n.dx = NIL
      n.symbol = NIL
      if character (tab[i],j) = "0"
         m.sx = n
         m = m.sx
      otherwise
         m.dx = n
         m = m.dx
   m.symbol = i
   m = B
2. Acquire the initial value of the signal:
   read/receive { x(1) }
3. Decode each string of bits input by traversing the
   tree B:
   for i = 1 , . . . , N-1
   read/receive { string }
   m = B
   for j = 1, . . . , length (string)
      if character (string, j) = "0"
         m = m.sx
      otherwise
         m = m.dx
```

-continued

```
y = m.symbol
x(i+1) = x(i) + y
```

It is worth stating that the notation used to describe the various steps of the method conforms to the following conventions:

The instruction blocks which are implemented in sequence are identified by indentation.

Selection conforms to the syntax:
   if condition
      block_1
   otherwise
      block_2

The sequence of instruction block_1 is implemented if the condition is true; block_2 is implemented if the condition is false.

Iterations are described by the notation for i=1, . . . , N meaning that the next block is implemented N times and that the variable i assumes the values 1, 2, 3, . . . , N in the course of the iterations.

The components of vectors and tables are indicated without distinction by the notation [] or ().

The function interrogations are indicated without distinction by the notation name_function () or name_function {}; any parameters are in parentheses and are separated by commas.

The components of the structures containing several fields are indicated with the use of the full stop as a separator: structure.component.

As can be seen, therefore, the method according to the present invention enables a high degree of compression to be achieved whilst at the same time being advantageously simple and inexpensive to implement.

Naturally, the principle of the invention remaining the same, the details of construction and forms of embodiment may be varied widely with respect to those described and illustrated, without thereby departing from the scope of the present invention.

What is claimed is:

1. A method of generating from an analog electroencephalographic signal a compressed signal for storing and/or transmitting the compressed signal, wherein said method comprises the following steps:
   converting the analog electroencephalographic signal into a signal in digital format,
   generating by means of an estimator predicted values of the digital signal on the basis of the past behavior of the analog signal and generating a signal indicative of the difference between predicted values and actual values of the digital signal, and
   encoding said signal indicative of the distance by means of variable-length codes with prefixes to generate the compressed signal.

2. A method according to claim 1, wherein the estimator generates a signal indicative of a first differential of the digital signal in order to generate the signal indicative of the distance between predicted values and actual values of the digital signal.

3. A method according to claim 1, wherein the method comprises the step of associating a conversion table with the compressed signal in the encoding stage.

4. A method according to claim 3, wherein the conversion table associates a string of binary numerals with each symbol present in the digital signal.

5. A method according to claim 3, wherein the conversion table is optimized on the basis of the relative frequencies of the symbols present in the entire digital signal.

6. A method according to claim 3, wherein the average relative frequencies of the symbols are estimated on a database containing sample digital electroencephalographic signals and the conversion table is an average conversion table obtained on the basis of the average relative frequencies.

7. A method according to claim 1, wherein the encoding stage uses a Huffman queue.

8. A method according to claim 7, wherein the Huffman queue uses a data structure of the type with a priority code.

9. A method according to claim 8, wherein said method comprises the steps of:

calculating a vector of the differences Y;

calculating frequencies of the symbols in Y;

inserting the symbols of Y in a priority queue H having frequency as a key;

constructing a binary tree B from said priority queue H;

traversing said tree B in pre-order thus constructing an encoding table tab; and creating a compressed signal including therein the table tab used for encoding and an initial value of the signal.

10. A method of decompressing a signal compressed by a compression method according to claim 7, wherein the compression method comprises the steps of:

reconstructing said binary tree B from said encoding table tab;

decoding strings of bits input by traversing said binary tree B; and reconstructing the compressed signal from symbols Y.

11. A method according to claim 6 wherein, said method comprises the steps of:

associating with said compressed signal said initial value of said electroencephalographic signal in digital format; and calculating the difference y and encoding the calculated difference Y.

12. A method of decompressing a signal compressed by the compression method according to claim 11, wherein the decompression method comprises the steps of:

constructing a binary tree from the encoding table tab;

acquiring an initial value of said electrocephalographic signal; and decoding strings of bits input by traversing said binary tree B.

* * * * *